US011905191B1

(12) United States Patent
Mjelde

(10) Patent No.: US 11,905,191 B1
(45) Date of Patent: *Feb. 20, 2024

(54) OZONE INJECTOR DEVICE

(71) Applicant: AquaStar Pool Products, Inc., Ventura, CA (US)

(72) Inventor: Olaf Mjelde, Ventura, CA (US)

(73) Assignee: AQUASTAR POOL PRODUCTS, INC., Ventura, CA (US)

( * ) Notice: Subject to any disclaimer, the term of this patent is extended or adjusted under 35 U.S.C. 154(b) by 167 days.

This patent is subject to a terminal disclaimer.

(21) Appl. No.: 17/577,295

(22) Filed: Jan. 17, 2022

Related U.S. Application Data

(63) Continuation-in-part of application No. 17/339,006, filed on Jun. 4, 2021, now Pat. No. 11,235,996, which
(Continued)

(51) Int. Cl.
C02F 1/78 (2023.01)
A61L 2/20 (2006.01)
(Continued)

(52) U.S. Cl.
CPC .............. *C02F 1/78* (2013.01); *A61L 2/202* (2013.01); *A61L 2/26* (2013.01); *B01F 23/232* (2022.01);
(Continued)

(58) Field of Classification Search
CPC ........ C02F 1/78; C02F 1/001; C02F 2103/42; C02F 2201/005; C02F 2201/782;
(Continued)

(56) References Cited

U.S. PATENT DOCUMENTS 2,367,606 A  1/1945 Olson
3,367,256 A  2/1968 Townsend et al.
(Continued)

FOREIGN PATENT DOCUMENTS

CA    508405     12/1954
EP   2277617    1/2011
(Continued)

OTHER PUBLICATIONS

How to Install the Del Spa Ozonator MCD-50, Sep. 24, 2010, YouTube, site visited Jul. 12, 2022 in related matter: https://www.youtube.com/ watch?v=-8vNlnL51Jg (Year: 2010); retrieved on Oct. 24, 2022 (4 pages).
(Continued)

*Primary Examiner* — Terry K Cecil
(74) *Attorney, Agent, or Firm* — Cislo & Thomas, LLP

(57) ABSTRACT

An ozone injector device comprising a housing, a corona tube disposed within the housing and configured to generate ozone, a check-valve having a first end removably coupled to the water passageway and a second end configured to receive ozone, the second end having a cavity with a movable float contained therein, an ozone inlet fitting removably coupled to the second end of the check-valve, the ozone inlet being in fluid communication with the corona tube via a corona discharge tube such that ozone entering the water passageway through the ozone inlet must pass through the check valve, and a spring-loaded clearing piston positioned to move into and out of the water passageway directly opposite the ozone inlet, the clearing piston being biased upwards, and configured to prevent flow of ozone into the water passageway.

10 Claims, 10 Drawing Sheets

Related U.S. Application Data is a continuation of application No. 17/187,505, filed on Feb. 26, 2021, now Pat. No. 11,084,745, which is a continuation-in-part of application No. 29/770,856, filed on Feb. 17, 2021, now Pat. No. Des. 972,069.

(51) Int. Cl.

| | | |
|---|---|---|
| *A61L 2/26* | (2006.01) | |
| *C01B 13/11* | (2006.01) | |
| *F04B 13/00* | (2006.01) | |
| *F04B 7/02* | (2006.01) | |
| *C02F 1/00* | (2023.01) | |
| *B01F 23/232* | (2022.01) | |
| *B01F 25/312* | (2022.01) | |
| *C02F 103/42* | (2006.01) | |
| *A61L 101/02* | (2006.01) | |
| *B01F 23/237* | (2022.01) | |
| *B01F 101/00* | (2022.01) | |

(52) U.S. Cl.
CPC .......... *B01F 25/312* (2022.01); *C01B 13/115* (2013.01); *C02F 1/001* (2013.01); *F04B 7/0266* (2013.01); *F04B 13/00* (2013.01); *A61L 2101/02* (2020.08); *A61L 2202/11* (2013.01); *B01F 23/237613* (2022.01); *B01F 2101/305* (2022.01); *C01B 2201/14* (2013.01); *C01B 2201/62* (2013.01); *C02F 2103/42* (2013.01); *C02F 2201/005* (2013.01); *C02F 2201/782* (2013.01); *C02F 2303/04* (2013.01)

(58) Field of Classification Search
CPC ........ C02F 2303/04; A61L 2/202; A61L 2/26; A61L 2101/02; A61L 2202/11; B01F 23/232; B01F 25/312; B01F 23/237613; B01F 2101/305; C01B 13/115; C01B 2201/14; C01B 2201/62; F04B 7/0266; F04B 13/00
See application file for complete search history.

(56) References Cited

U.S. PATENT DOCUMENTS

| | | | |
|---|---|---|---|
| 3,511,268 | A | 5/1970 | Dubrovsky et al. |
| D231,823 | S | 6/1974 | Sharp |
| 4,019,986 | A | 4/1977 | Burris et al. |
| 4,336,820 | A | 6/1982 | Jorgensen et al. |
| 4,545,221 | A | 10/1985 | Daniel et al. |
| D290,632 | S | 6/1987 | Dehnert et al. |
| D307,460 | S | 4/1990 | Bradford |
| 5,081,328 | A | 1/1992 | Friend et al. |
| 5,503,742 | A | 4/1996 | Farley |
| 5,509,349 | A | 4/1996 | Anderson et al. |
| D440,265 | S | 4/2001 | Cannon |
| D535,352 | S | 1/2007 | Verdon |
| D586,347 | S | 2/2009 | Cheng |
| D597,172 | S | 7/2009 | Hin |
| D634,397 | S | 3/2011 | Lautzenheiser |
| D692,524 | S | 10/2013 | Ziser |
| D725,204 | S | 3/2015 | Rub |
| 9,205,386 | B2 | 12/2015 | Wu |
| 9,352,989 | B2 | 5/2016 | Lacasse |
| D768,031 | S | 10/2016 | Pellham |
| 9,616,435 | B2 | 4/2017 | Smith et al. |
| D791,768 | S | 7/2017 | Billard |
| 9,863,379 | B2 | 1/2018 | Heinrich et al. |
| D857,838 | S | 8/2019 | Pitman |
| 10,669,171 | B2 | 6/2020 | Heng |
| D890,295 | S | 7/2020 | Xu et al. |
| 10,717,047 | B1 | 7/2020 | Wang |
| D897,492 | S | 9/2020 | Pitman |
| 11,019,827 | B1 | 6/2021 | Lynn |
| 11,084,745 | B1 | 8/2021 | Mjelde |
| 11,235,996 | B1 | 2/2022 | Mjelde |
| D951,392 | S | 5/2022 | Uemori |
| 11,345,623 | B1 | 5/2022 | Mjelde |
| 11,358,888 | B1 | 6/2022 | Mjelde |
| D972,069 | S | 12/2022 | Mjelde |
| 11,518,697 | B1 | 12/2022 | Mjelde |
| 2002/0127158 | A1 | 9/2002 | Holsclaw et al. |
| 2003/0183585 | A1 | 10/2003 | Cho |
| 2013/0105373 | A1 | 5/2013 | Chen et al. |
| 2015/0203376 | A1 | 7/2015 | Heng |
| 2016/0152497 | A1 | 6/2016 | Tandon |
| 2018/0193507 | A1 | 7/2018 | Tapp et al. |
| 2019/0084852 | A1 | 3/2019 | Harris |
| 2019/0195370 | A1 | 6/2019 | Huang |
| 2020/0271635 | A1 | 8/2020 | Key et al. |
| 2022/0340457 | A1 | 10/2022 | Thompson |

FOREIGN PATENT DOCUMENTS

| | | |
|---|---|---|
| GB | 476141 | 12/1937 |
| KR | 20020012974 | 2/2020 |

OTHER PUBLICATIONS

Results of the Aero-Spa System, Jun. 18, 2015, YouTube, site visited Jul. 12, 2022 in related matter: https://www.youtube.com/watch?v= z_fq1AebY_A (Year: 2015); retrieved on Oct. 24, 2022 (4 pages).

CircuPool CORE35 Salt Chlorinator System, Oct. 12, 2019, Amazon, site visited Mar. 8, 2023: https://www.amazon.ca/dp/ B07PVL1R25/ (Year: 2019); in related matter (U.S. Appl. No. 29/868,504) on Mar. 21, 2023; retrieved on Mar. 21, 2023 via https://www.amazon.com/Circupool-Chlorinator-Warranty-Electronic-Generator/dp/B07PVL1R25?source=ps-sl-shoppingads-lpcontext&ref_=fplfs&psc=1&smid=AMGPO4TTUWNSH (8pg).

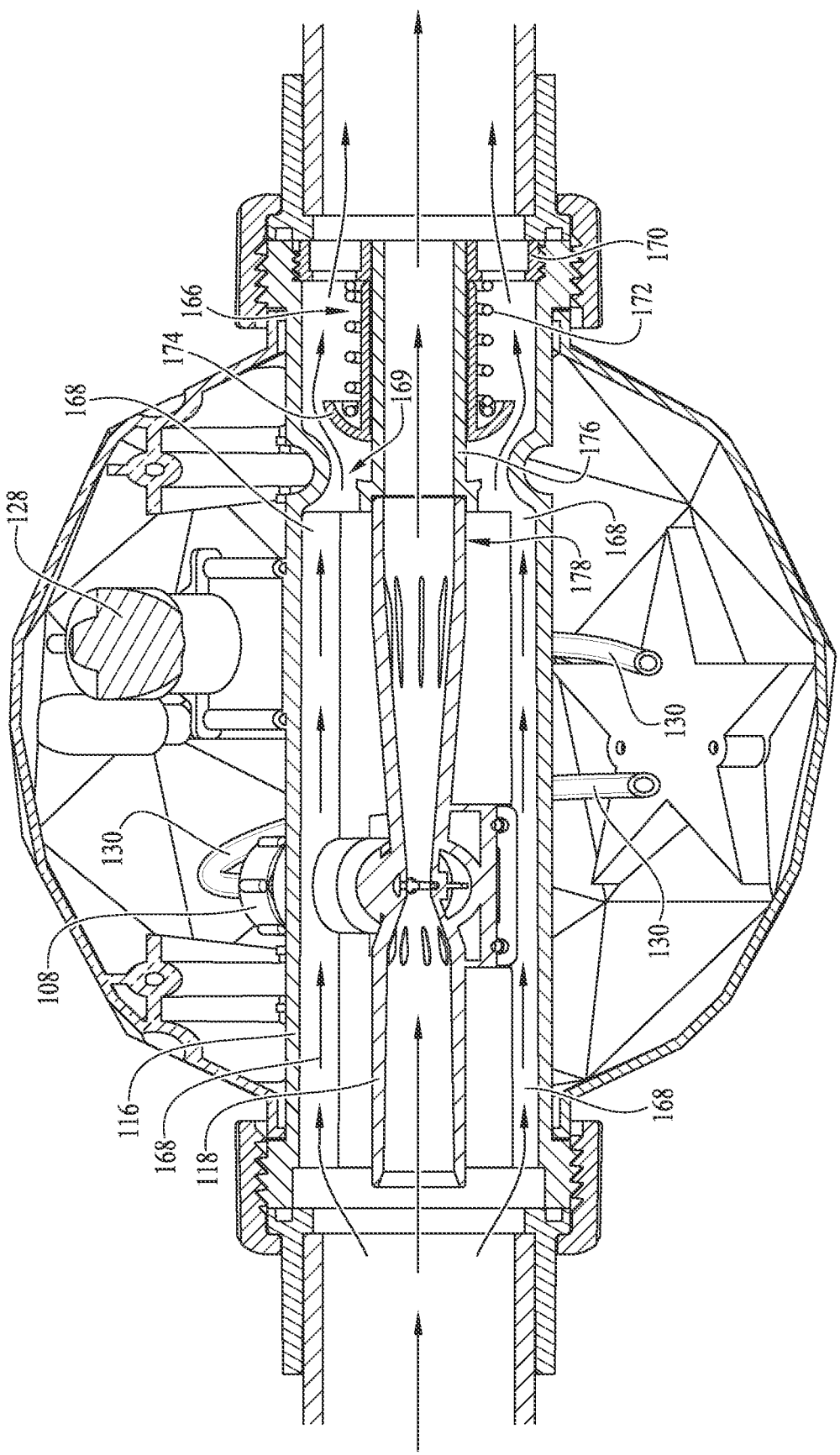

OZONE INJECTOR DEVICE

CROSS-REFERENCE TO RELATED APPLICATION

This application is a Continuation of U.S. Non-Provisional patent application Ser. No. 17/339,006, now U.S. Pat. No. 11,235,996, titled "Ozone Injector Device," filed Jun. 4, 2021, which is a Continuation of U.S. Non-Provisional patent application Ser. No. 17/187,505, now U.S. Pat. No. 11,084,745, titled "Ozone Injector Device," filed Feb. 26, 2021, which is a Continuation-In-Part of U.S. Design patent application Ser. No. 29/770,856, titled "Ozone Injector Device," filed Feb. 17, 2021, the contents of which are incorporated herein by reference in their entirety.

BACKGROUND

Ozone is a powerful oxidizing agent which, when dissolved in water, produces a broad spectrum biocide that destroys all bacteria, viruses and cysts. It is useful for water treatment, but known ozone injector systems require multiple different components and suffer from calcium buildup which significantly reduces the effectiveness of the system.

Accordingly, there is a need for an improved device/system for injecting ozone into water as a means of water treatment.

SUMMARY

In the invention described herein is directed to my ozone injector device. The device has a housing, a corona tube, a check-valve, an ozone inlet, and a spring-loaded clearing piston.

The housing has a water passageway through the housing. The housing can be formed by two removable halves, and the water passageway can be a venturi.

The corona tube is disposed within the housing and configured to generate ozone.

The check-valve has a first end removably coupled to the water passageway and a second end configured to receive ozone. The second end has a cavity with a movable float contained therein.

The ozone inlet fitting is removably coupled to the second end of the check-valve. The ozone inlet is in fluid communication with the corona tube via a corona discharge tube such that ozone entering the water passageway through the ozone inlet must pass through the check valve.

The spring-loaded clearing piston is positioned to move into and out of the water passageway directly opposite the ozone inlet. The piston is biased upwards, towards to the ozone inlet, and configured to prevent flow of ozone into the water passageway and to prevent flow of water into the corona discharge tube.

Optionally, the housing has an air inlet with a removable cover and a fuse holder positioned along an exterior surface of the housing.

Optionally, the piston is positioned to insert into the water passageway at the water passageway's narrowest point.

The spring loaded clearing piston can comprise a lower housing coupled to an exterior surface of the water passageway that forms a lower cavity that is in fluid communication with the water passageway by a pressure inlet and a pressure outlet. Pressure changes in the water passageway induce the piston to move between a flow position and a no-flow position.

When the piston is in the flow position, the piston is depressed downward, away from the valve seat such that ozone can enter the water passageway.

When the piston is in the no-flow position, the piston is spring-biased upwards, and ozone is prevented from entering the water passageway and water is prevented from entering the corona discharge tube.

The spring-loaded piston can comprise a spring positioned within the lower cavity, below the piston, to spring-bias the piston upwards. This prevents water from entering the corona discharge tube and prevents ozone from entering the water passageway.

Optionally, the corona discharge tube forms a Hartford loop between the corona tube and the ozone inlet fitting.

Optionally, a high-voltage transformer is disposed within the housing and electrically coupled to a power source.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIG. 10 is an additional side sectional view of the ozone injector device of FIG. 1 taken along line 6-6, wherein an overflow position is shown;

DETAILED DESCRIPTION

Figure 1:
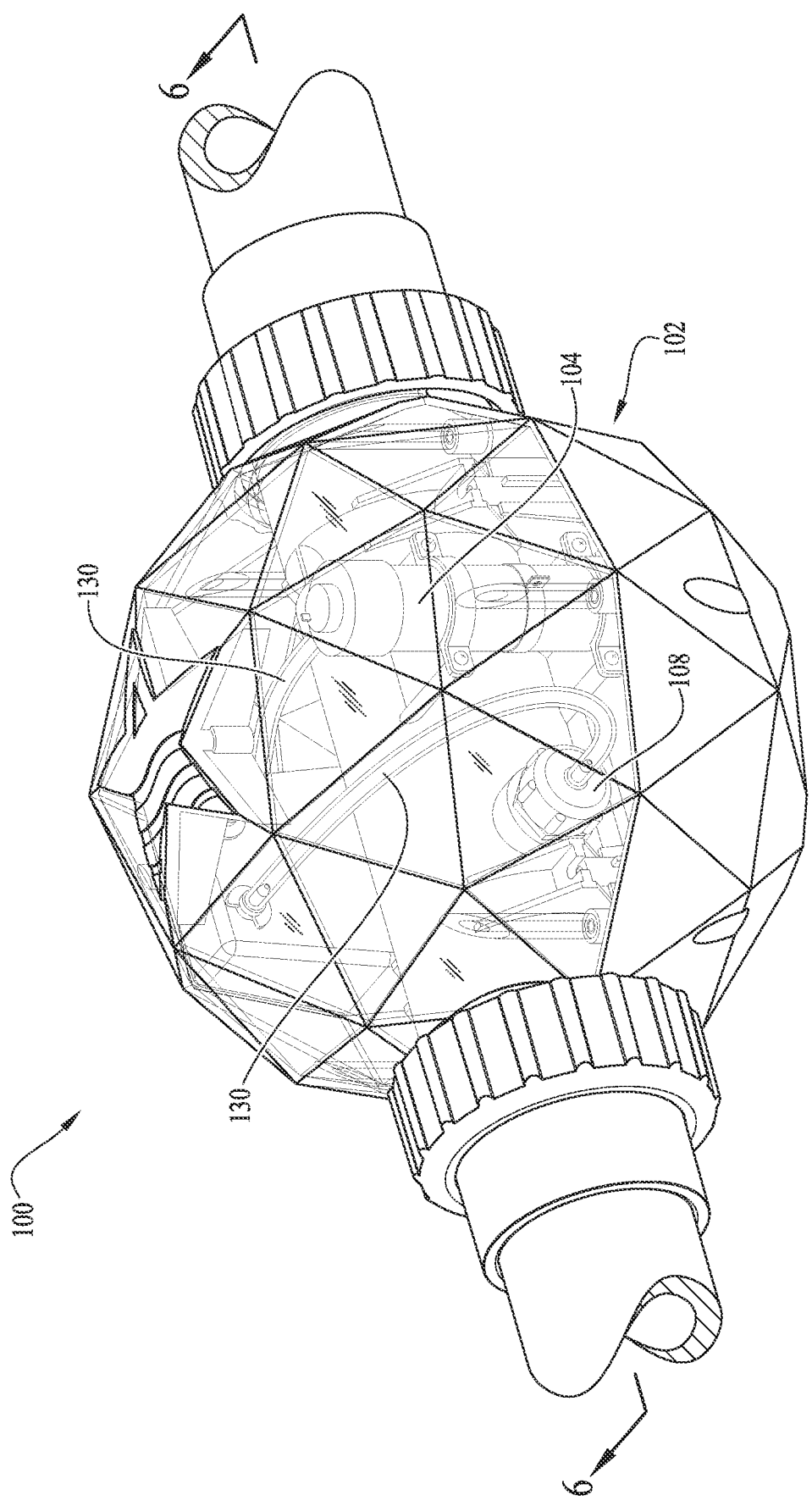
FIG. 1 is a top perspective view of my ozone injector device.

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," are not intended to exclude other additives, components, integers ingredients or steps.

All dimensions specified in this disclosure are by way of example only and are not intended to be limiting. Further, the proportions shown in these Figures are not necessarily to scale. As will be understood by those with skill in the art with reference to this disclosure, the actual dimensions and proportions of any system, any device or part of a device disclosed in this disclosure will be determined by its intended use.

All uses of positioning terms such as "upwards" and "downwards" in this disclosure are not limiting and are used only to describe the relation of the various components to each other when the device is in its typical operating positon/orientation. However, because the position/orientation of the device may vary, the meaning of "upwards" and "downwards" may vary depending on the position/orientation of the device.

Referring now to the drawings, like reference numerals designate identical or corresponding features throughout the several views. Further, described herein are certain non-limiting embodiments of my pipeline filter assembly for pool filtering and maintenance.

Referring to FIGS. 1 through 5, there is shown one embodiment of my ozone injector device 100. The device has a housing 102, a corona tube 104, a check-valve 106, an ozone inlet 108, and a spring-loaded clearing piston 110.

The housing 102 has a water inlet 112 and a water outlet 114 in fluid communication with each other and forming a main water passageway 116 through the housing. Optionally, the housing 102 can be formed by two halves 102A, 102B removably coupled together by a plurality of fasteners 105. The main water passageway can have a venturi 118 located therein which is best seen in FIGS. 5 through 10. The water inlet 112 and the water outlet 114 can be configured to couple to a water filtration system for a pool or spa.

Figure 2:
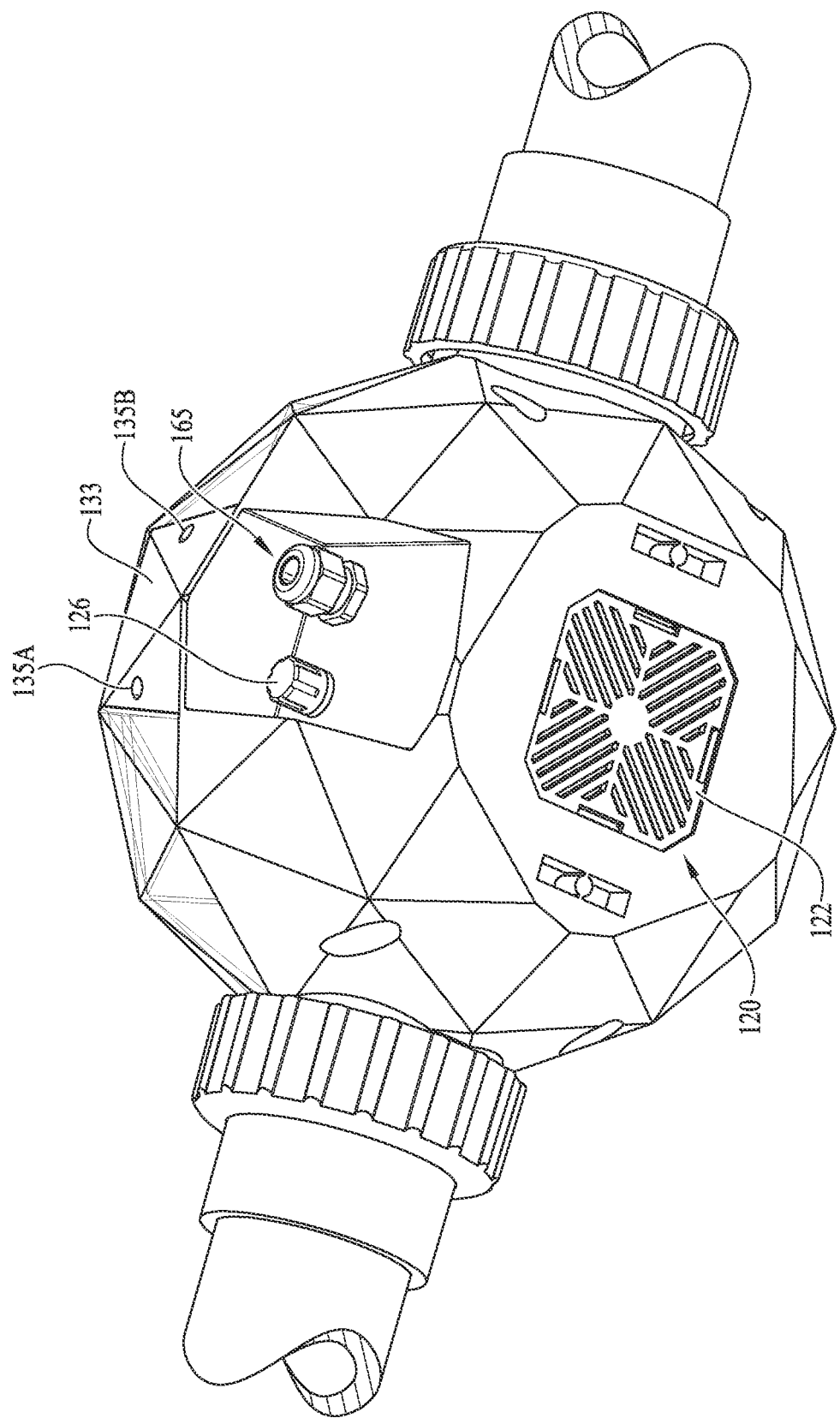
FIG. 2 is a bottom perspective view of my ozone injector device of FIG. 1.
Figure 3:
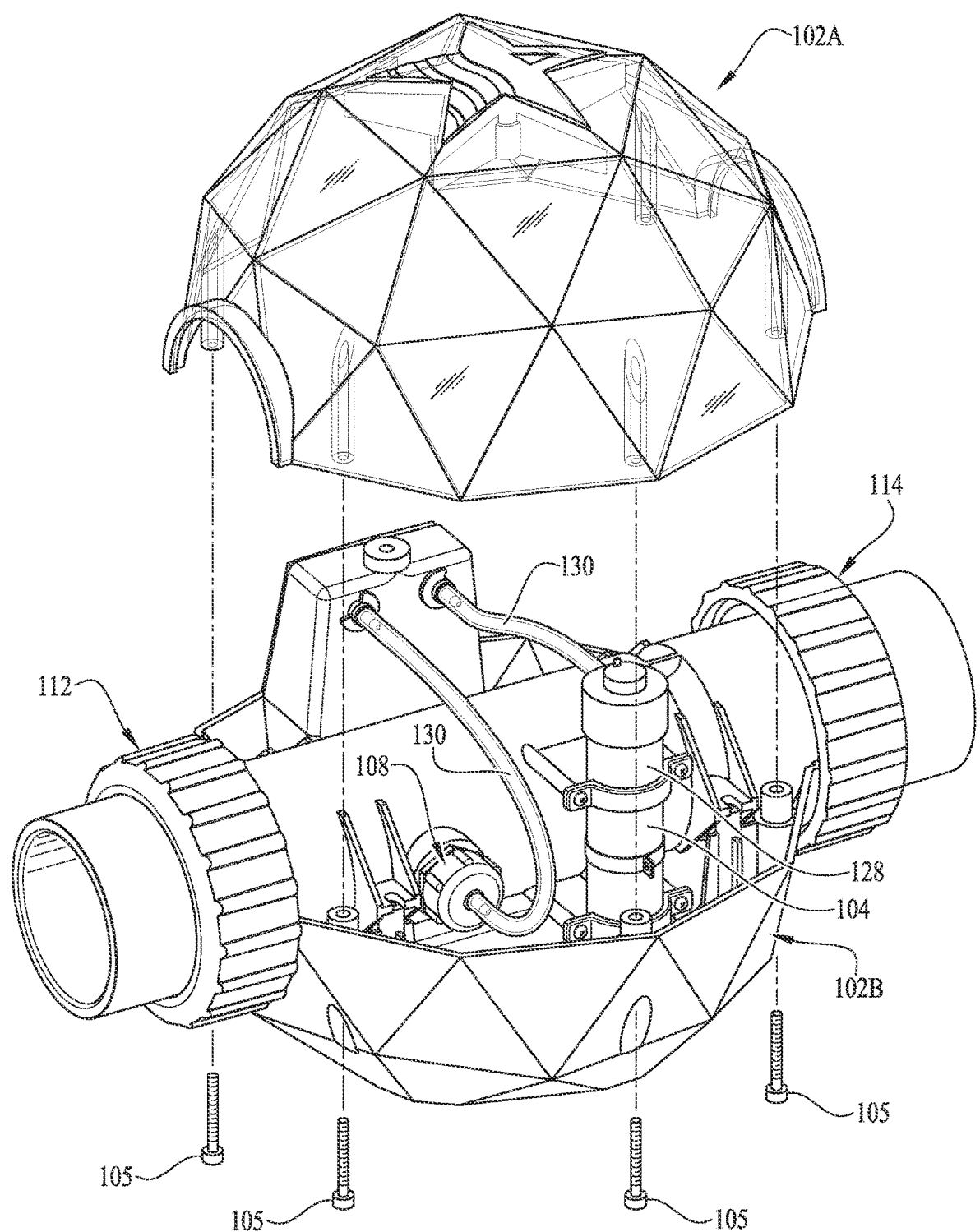
FIG. 3 is an additional perspective view of the ozone injector device of FIG. 1, wherein the top half of the housing has been removed.
Figure 4:
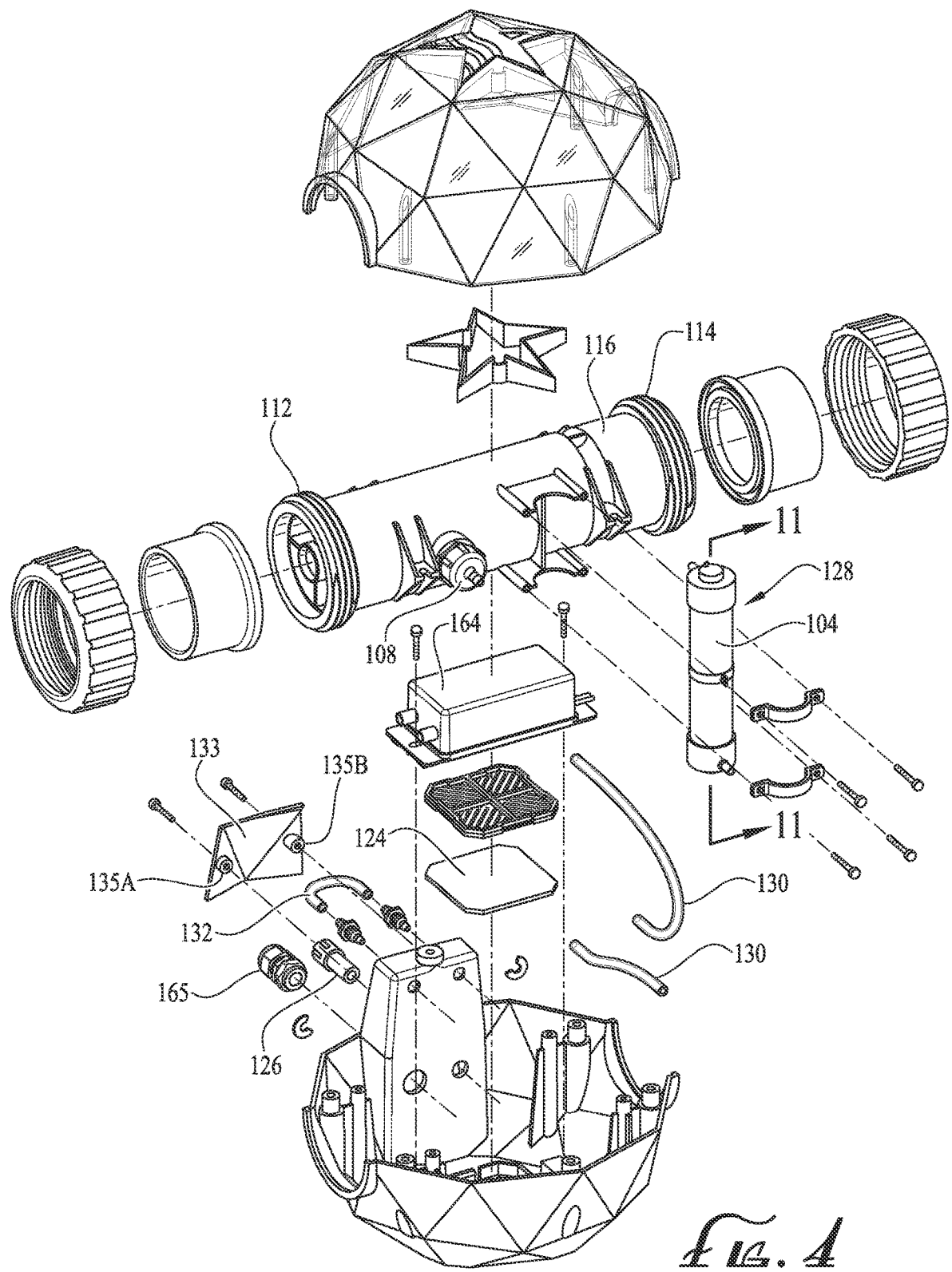
FIG. 4 is an exploded view of my ozone injector device.

As best seen in FIGS. 2 and 4, the housing 102 can have an air inlet 120 with a removable cover 122. There can be a removable air filter 124 disposed within the air inlet 120, behind the removable cover 122. The air filter 124 is to ensure that no air leaving the housing 102 contains ozone vapors.

The housing 102 can also have a fuse holder 126 positioned along an exterior surface of the housing 102. The fuse holder 126 is configured to receive and retain a fuse. The fuse protects the device 100 from being damaged during a sure in electricity.

The corona tube 104 is disposed within the housing 102 and configured to generate ozone. Preferably, the corona tube 104 has a longitudinal axis that is perpendicular to a longitudinal axis of the main water passageway 116 such that an upper portion 128 of the corona tube 104 is positioned above the ozone inlet 108 of the main water passageway 116. This configuration ensures that liquid (ozone) in the corona tube 104 travels downward and out of the ozone inlet 108 and into the water passageway 116.

Figure 11:
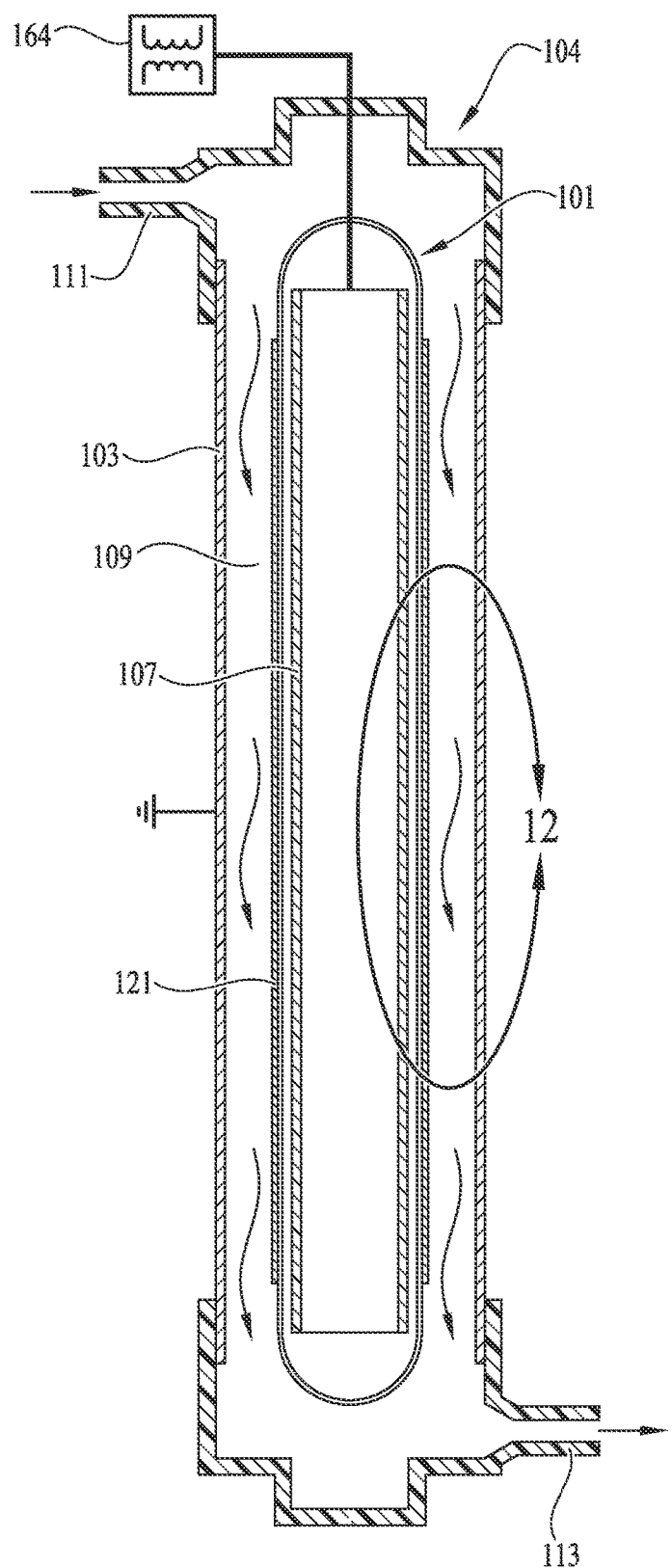
FIG. 11 is a sectional view of the ozone tube shown in FIG. 4, taken along line 11-11, wherein the flow of generated ozone within the ozone tube is shown via the arrows.
Figure 12:
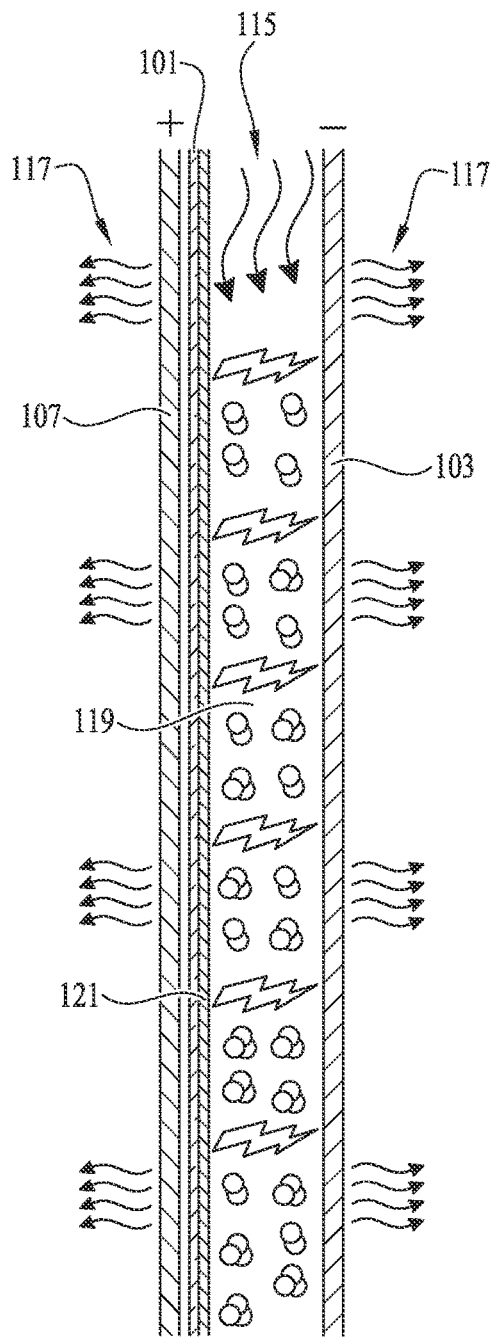
FIG. 12 is an enlarged view of a portion of the ozone tube of FIG. 11.

The ozone tube 104 is shown in greater detail in FIGS. 11 and 12. The tube 104 comprises an outer casing 103, an inner glass or quartz tube 101 is made from quartz, and there is a metallic tube 107 disposed within the inner glass tube 101 forming a space 109 therebetween. Outer casing 103 has a gas input 111 and a gas output 113. The transformer 164 is electrically coupled to the metallic tube 107. A gas 115 that is an oxygen source (either air or pure oxygen gas) passes through the space 109 formed between an outer surface of the glass tube 101 and an inner surface of the outer casing 103. Because the metallic tube 107 is electrically charged (via the transformer 164), ozone 117 is formed in the space 109 and leaves the casing 103 via the gas output 113. There is a dielectric 121 along an outer surface of the glass tube 107 that assists in diffusing electrical discharge from the transformer 164 over the glass tube 107. The dielectric 121 can be stainless steel or aluminum.

Preferably, there is a corona discharge tube 130 that connects the corona tube output 113 to the ozone inlet 108. Optionally, the corona discharge tube 130 forms a Hartford loop 132 between the corona tube 104 and the ozone inlet fitting 108. The Hartford loop 132 allows the device 100 to be installed below the pool water line. If a Hartford loop 132 is used, then the loop 132 must be run outside the device 100, above the pool water line, and back into the device 100. To that end, a loop door 133 is provided on the outside of the device 100, which is best seen in FIG. 2. The loop door 133 has two ports 135A, 135B to allow the loop 132 to exit and re-enter the device 100. The loop ports 135A, 135B can also be used to cap the ozone discharge tube 130 to pressure test the device 100.

Figure 7:
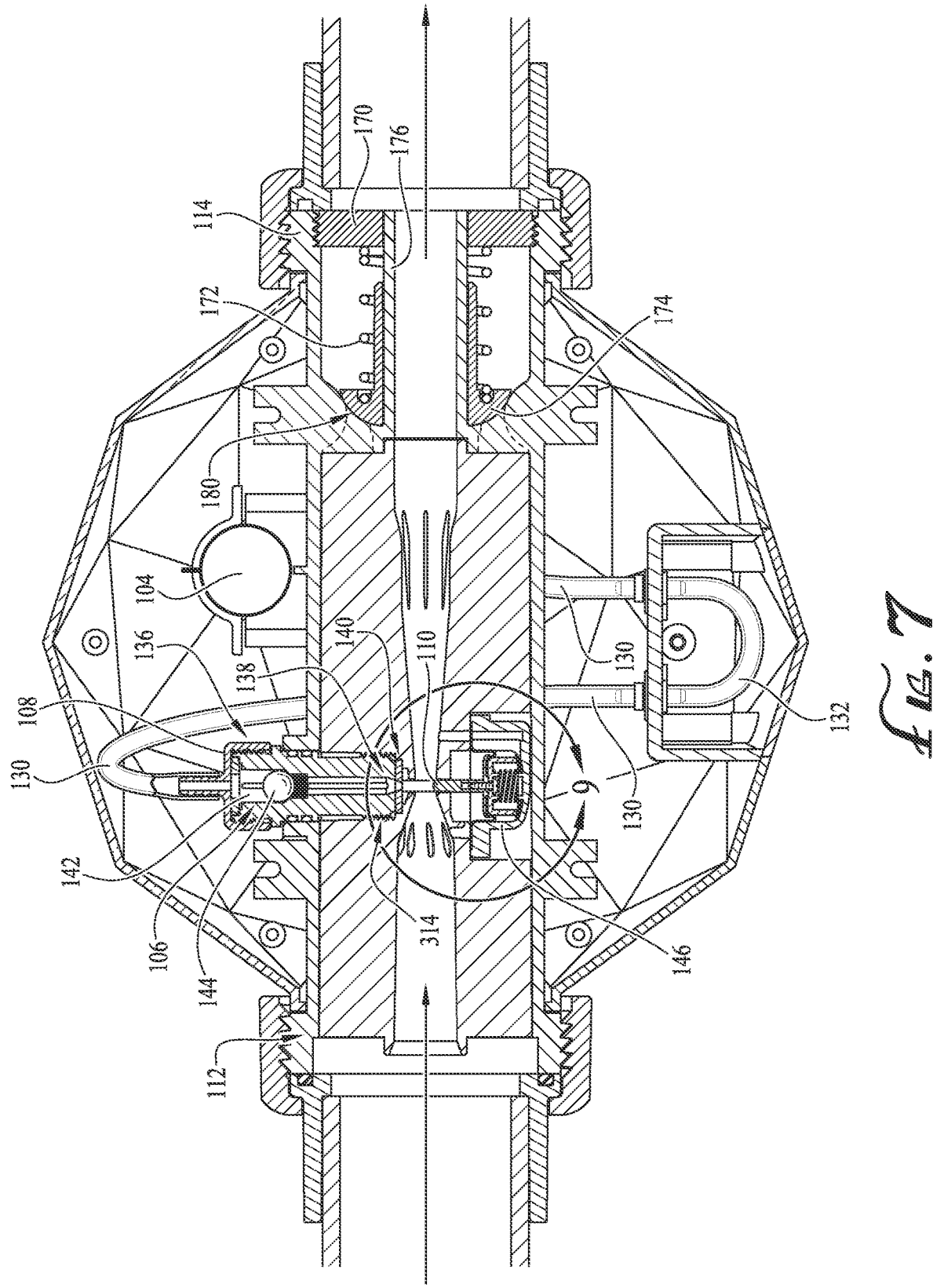
FIG. 7 is a sectional side view of my ozone injector device, wherein the clearing piston is in the flow position.

The check-valve 106 is best seen in FIG. 7 and has a first end 134 and a second end 136. The first end 134 is removably coupled to the main water passageway 116 and has an outlet 138 with a valve seat 140. Preferably the first end 134 of the check-valve 106 is threadedly coupled to the main water passageway 116.

The second end 136 of the check-valve 106 is configured to receive ozone from the ozone discharge tube 130 and has a cavity 142 with a movable float 144 contained therein. Typically, the float 144 is in the form of a ball, forming a standard ball check-valve 106. The check-valve 106 prevents water from back-flowing into the ozone discharge tube 130. The check-valve 106 also comprises a pair of O-rings 145 and a pair of valve seats 147, one upper and one lower, for the float 144 to seal against.

The ozone inlet fitting 108 is removably coupled to the second end 136 of the check-valve 106. The ozone inlet 108 is in fluid communication with the corona tube 104 via the corona discharge tube 130 such that ozone entering the main water passageway 116 through the ozone inlet 108 must pass through the check-valve 106.

The spring-loaded clearing piston 110 is best seen in FIGS. 6 through 10 and is positioned to move into and out of the main water passageway 116 directly opposite the ozone inlet 108. The piston 110 is biased upwards, towards to the ozone inlet 108, and when pressed against the valve seat 140, is configured to prevent flow of ozone into the main water passageway 116 and to prevent flow of water into the corona discharge tube 130. If the main water passageway 116 is or has a venturi 118, the piston 110 is positioned to insert into the main water passageway 116 at the main water passageway's 116 narrowest point. This can be seen in FIGS. 6 through 10.

Figure 5:
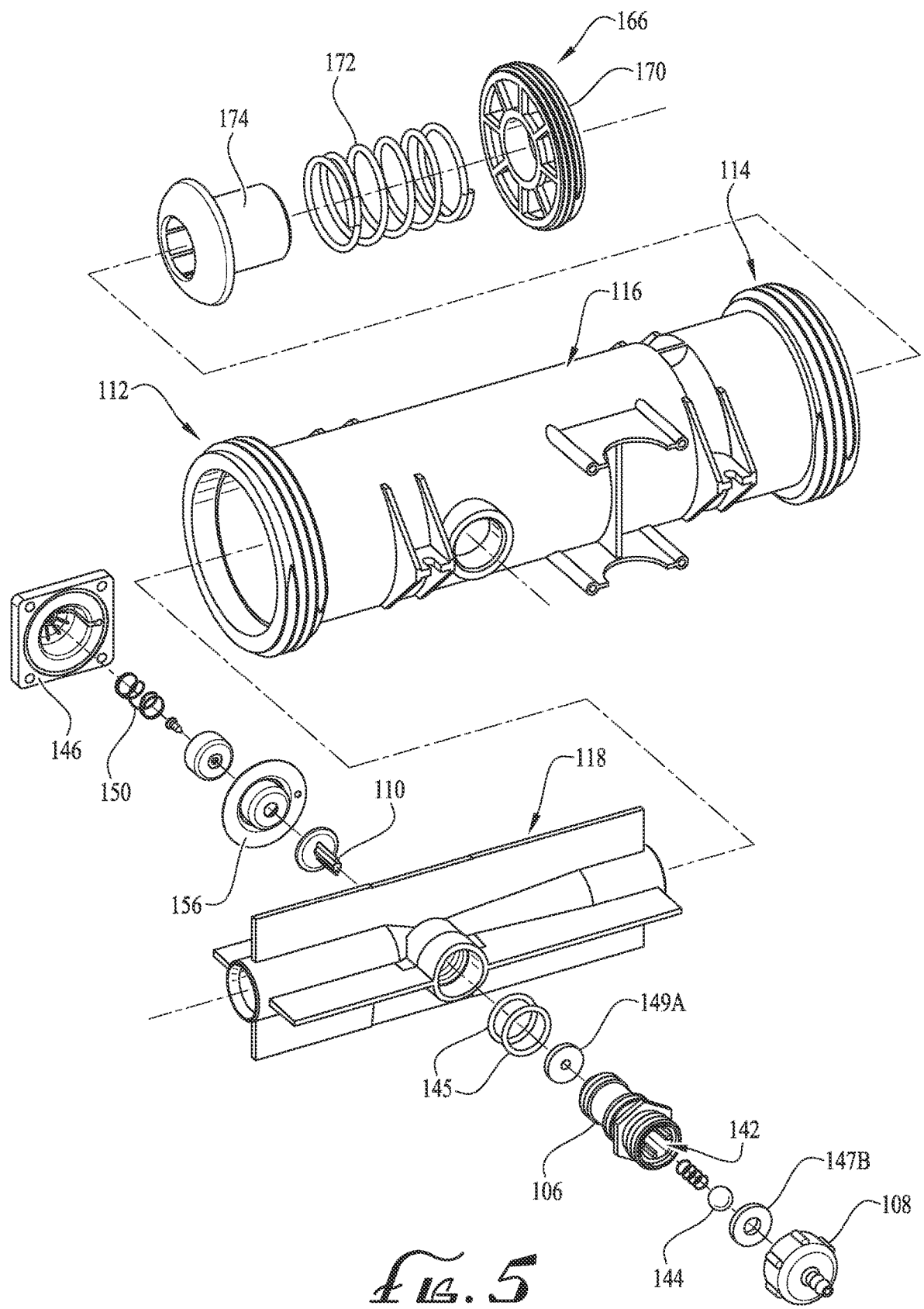
FIG. 5 is an additional exploded view of a portion of my ozone injector device.
Figure 9:
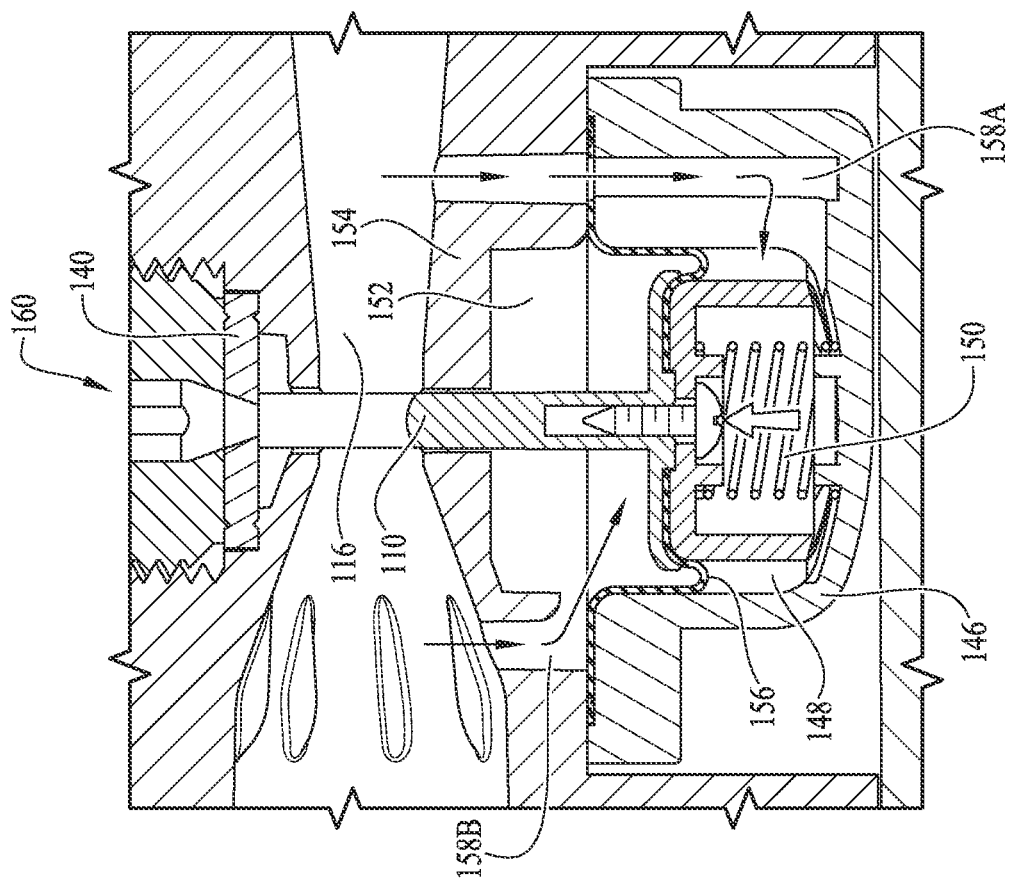
FIG. 9 is an enlarged view of a portion of FIG. 6.
Figure 8:
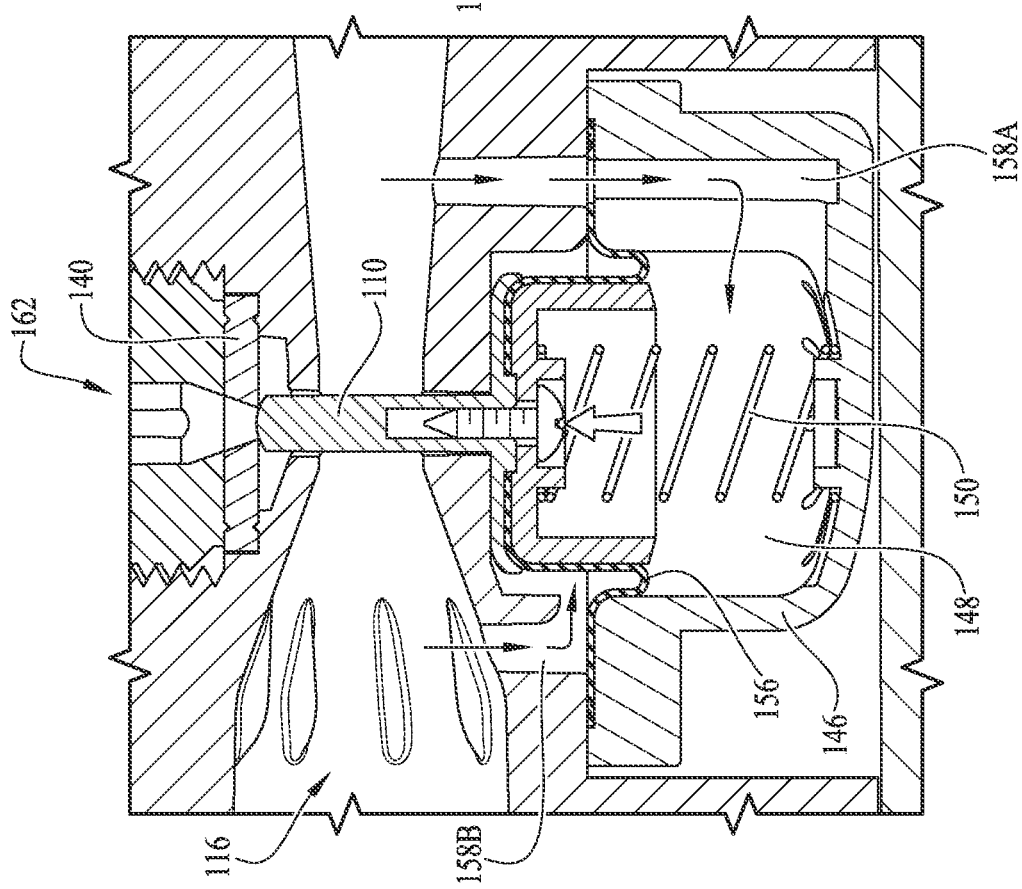
FIG. 8 is an enlarged view of a portion of FIG. 5.

As best seen in FIGS. 5, 8 and 9, the spring loaded clearing piston 110 can comprise a lower housing 146 coupled to an exterior surface of the main water passageway 116, forming a lower cavity 148. There can be a spring 150 positioned within the lower cavity 148, below the piston 110, to spring-bias the piston 110 upwards and into contact with the valve seat 140 of the check-valve 106. This prevents water from entering the corona discharge tube 130 and prevents ozone from entering the main water passageway 116. The clearing piston 110 also provides the added advantage of clearing calcium buildup from ozone injector port (valve seat 140), as this a known point of failure in prior art ozone injector devices.

As best seen in FIG. 9, preferably, there is an upper cavity 152 disposed within a side surface 154 of the main water passageway 116 that mates with the lower cavity 148. The piston 110 is positioned within the cavities 148, 152, and the upper cavity 152 and the lower cavity 148 are divided by a flexible diaphragm 156 that is coupled to and moves with the piston 110.

As best seen in FIGS. 8 and 9, both the upper cavity 152 and the lower cavity 148 are in fluid communication with the main water passageway 116 via their own pressure adjustment passageway 158A, 158B. Pressure changes in the main water passageway 116 induce the piston 110 to move between a flow position 160 and a no-flow position 162.

The no-flow position 162 is shown in FIG. 8. When the piston 110 is in the no-flow position 162, the piston 110 is spring-biased upwards, against the valve seat 140, and ozone is prevented from entering the water passageway 116 and water is prevented from entering the corona discharge tube 130. Water pressure in the lower cavity 148 being greater than water pressure in the upper cavity 152 induces the piston 110 to be positioned in the no-flow position 162. Stated another way, the water pressure entering the water passageway 116 is les than the water pressure leaving the water passageway 116, and the upward force of the spring 150 has not been overcome. This no-flow position 162 is the naturally biased positon of the piston 110 due to the spring 150 under the piston 110 constantly pushing the piston 110 upwards.

The flow position 160 is shown in FIG. 9. When the piston 110 is in the flow position 160, the piston 110 is depressed downward, away from the valve seat 140 such that ozone can enter the water passageway 116. This is caused by water pressure in the upper cavity 152 being greater than water pressure in the lower cavity 148 and overriding the upward pressure of the spring 150 below the piston 110. Stated another way, the water pressure entering the water passageway 116 is greater than the water pressure leaving the water passageway 116.

Optionally, a high-voltage transformer 164 is disposed within the housing 102 and can be electrically coupled to a power source. The power source can be either internal to the device 100 or external to the device 100. If the power source is external, there is a power cord port 165 in the side of the housing 102.

Figure 6:
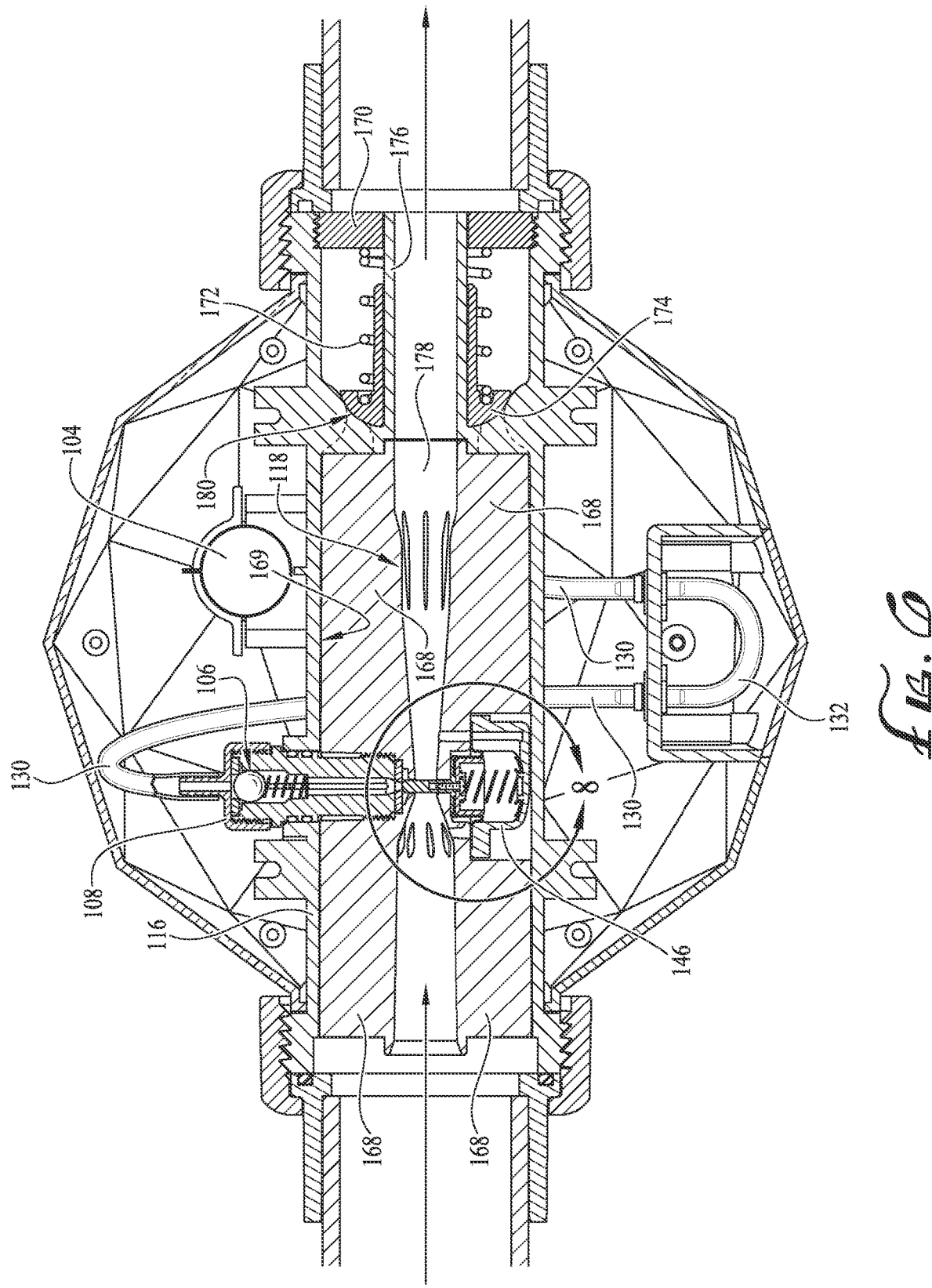
FIG. 6 is a sectional side view of my ozone injector device of FIG. 1 taken along line 6-6, wherein the clearing piston is in the no-flow position.

If the device 100 has a venturi 118 located/formed within the main water passageway 116, then the device 100 can also comprise a bypass valve 166 and form water bypass passageways 168 between an exterior surface of the venturi 118 and an interior surface 169 of the main water passageway 116. These components are best seen in FIGS. 5 and 10. If the water flow increases to a point where the restriction through the center of the venturi 118 creates too much back pressure, the bypass valve 166 will open and allow water to flow around the venturi 118. The bypass valve 166 is located proximate the water outlet 114 of the device 100 and comprises a base 170, a spring 172, and a poppet 174. There is a tubular extension 176 that extends an outlet 178 of the venturi to be in approximately in line with the outlet 114 of the water passageway 116. The base 170 is threadedly coupled to an interior of the water outlet 114, with the extension 176 passing through a center of the base 170. The spring 172 and the poppet 174 are slidably positioned around the extension 176, such that the spring 172 that is applying an outward pressure against both the poppet 174 and the base 170. This pressure causes the poppet 174 to seal against a valve seat 180 formed between the extension 176 and the interior surface 169 of the water passageway 116. When the poppet 174 is pressed against the valve seat 180, the bypass valve 166 is in the closed position. The bypass valve 166 closed positon is best seen in FIGS. 6 and 7.

When the pressure becomes too great, and the biasing pressure of the spring 172 can be overcome, the poppet 174 is then forced away from the valve seat 180, allowing water to flow around the exterior of the venturi 118, through the water bypass passageways 168, and out the water outlet 114 of the device 100. The bypass valve 166 begins to open at approximately 25 GPM (gallons per minute). This is the open position of the bypass valve 166, and is best shown in FIG. 10. The flow of water through the bypass passageways 168 is shown with the arrows. The spring 172 is interchangeable, meaning, a user can use different springs 172 having different strengths to adjust the pressure threshold required to open the bypass valve 166.

The ozone injector device 100 may be constructed from subparts made by injection mold. The injection mold process may use a variety of plastics known in the industry, for example, PVC. Subsequent to molding said subparts, the subparts may then be glued to a standard pipe sufficient for pool filtering uses, for example, schedule 40 PVC pipe or other types of pipe. Construction by injection mold of smaller subparts means that overly large injection molds are not required, and thus savings may be had during construction and then passed to end consumers.

The device 100 is used by coupling the device 100 to a pool or spa filter system and dispensing ozone to the water flowing through the device 100. The device 100 self-regulates the dispensing of the ozone so no user input is needed for the device 100 to perform its normal daily functions.

The ozone injector device 100 of the present invention has many advantages, including but not limited to.

The device 100 is an all-in-one, self-contained water ozone treatment system. There is no need for a separate ozone generator and/or injector.

The clearing piston 110 automatically cleans calcium buildup from the ozone injector port (valve seat 140), and this is a well-known point of failure for existing ozone injector systems.

The integrated bypass valve 166 regulates water flow through the center of the venturi 118 which then, by default, also regulates the flow of ozone into the venturi 118.

The spring 172 that is part of the bypass valve 166 can be changed to adjust the pressure threshold at which the bypass valve 166 opens.

The Hartford loop 132 allows for the ozone device 100 to be installed below the pool water line.

The check-valve 106 prevents water from flowing into the ozone discharge tube 130.

A ozone shut off valve is formed by the biasing of the piston 110 against valve seat 140. This is a hard shut off valve that blocks the ozone flow port when the device 100 is turned off. This prevents water from leaking past the check-valve 106 and into the ozone discharge tube 130 while the device 100 is shut off.

While particular forms of the invention have been illustrated and described, it will also be apparent to those skilled in the art that various modifications can be made without departing from the spirit and scope of the invention.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference.

What is claimed is:

1. An ozone injector device comprising:
   a) a housing formed by two halves removably coupled together, the housing having:

i) a water passageway through the housing, wherein the water passageway is a venturi having a water inlet and a water outlet configured to couple to a water filtration system for a pool or spa;

b) a corona tube disposed within the housing and configured to generate ozone;

c) a high-voltage transformer disposed within the housing and configured to electrically couple to a power source;

d) a check-valve having a first end removably coupled to the water passageway and a second end configured to receive ozone, the second end having a cavity with a movable float contained therein;

e) an ozone inlet fitting removably coupled to the second end of the check-valve, the ozone inlet fitting being in fluid communication with the corona tube via a corona discharge tube such that ozone entering the water passageway through the ozone inlet fitting must pass through the check valve; and f) a spring-loaded clearing piston positioned to move into and out of the water passageway directly opposite the ozone inlet fitting, the clearing piston being biased upwards, towards the ozone inlet fitting, and configured to prevent flow of ozone into the water passageway.

2. An ozone injector device comprising:

a) a housing having a water passageway through the housing;

b) a corona tube disposed within the housing and configured to generate ozone;

c) a check-valve coupled to the water passageway and configured to receive ozone;

d) an ozone inlet fitting removably coupled to the check-valve, the ozone inlet fitting being in fluid communication with the corona tube via a corona discharge tube such that ozone entering the water passageway through the ozone inlet fitting must pass through the check valve; and e) a spring-loaded clearing piston positioned to move into and out of the water passageway directly opposite the ozone inlet fitting, the clearing piston being biased upwards, towards the ozone inlet fitting, and configured to prevent flow of ozone into the water passageway.

3. The device of claim 2, wherein the device housing is formed by two halves removably coupled together.

4. The device of claim 2, wherein the water passageway is a venturi.

5. The device of claim 2, further comprising:

i) an air inlet with a removable cover positioned along an exterior surface of the housing; and ii) a fuse holder positioned along the exterior surface of the housing.

6. The device of claim 2, wherein the piston is positioned to insert into the water passageway at the water passageway's narrowest point.

7. The device of claim 2, wherein the spring loaded clearing piston comprises a lower housing coupled to an exterior surface of the water passageway and forming a lower cavity that is in fluid communication with the water passageway by a pressure inlet and a pressure outlet, such that pressure changes in the water passageway induce the piston to move between a flow position and a no-flow position.

8. The device of claim 7, wherein when the piston is in the flow position, the piston is depressed downward, such that ozone can enter the water passageway.

9. The device of claim 7, wherein when the piston is in the no-flow position, the piston is spring-biased upwards, and ozone is prevented from entering the water passageway and water is prevented from entering the corona discharge tube.

10. The device of claim 7, wherein the spring-loaded clearing piston comprises a spring positioned within the lower cavity, below the piston, to spring-bias the piston upwards, thereby preventing water from entering the corona discharge tube and preventing ozone from entering the water passageway.

* * * * *